(12) United States Patent
Heath et al.

(10) Patent No.: US 10,813,714 B2
(45) Date of Patent: Oct. 27, 2020

(54) SYSTEMS AND METHODS FOR VISUAL STAGING OF MEDICAL DEVICES

(71) Applicant: Aesthetic Practice Solutions, LLC, Whitefish Bay, WI (US)

(72) Inventors: Ryan Heath, Whitefish Bay, WI (US); Dawn Sagrillo, Pewaukee, WI (US)

(*) Notice: Subject to any disclaimer, the term of this patent is extended or adjusted under 35 U.S.C. 154(b) by 187 days.

(21) Appl. No.: 15/994,423

(22) Filed: May 31, 2018

(65) Prior Publication Data
US 2019/0365495 A1 Dec. 5, 2019

(51) Int. Cl.
| A61B 50/00 | (2016.01) |
| A61B 50/20 | (2016.01) |
| A61B 50/10 | (2016.01) |
| A61B 90/60 | (2016.01) |
| A61B 50/30 | (2016.01) |

(52) U.S. Cl.
CPC .............. *A61B 50/20* (2016.02); *A61B 50/10* (2016.02); *A61B 90/60* (2016.02); *A61B 50/30* (2016.02)

(58) Field of Classification Search
CPC ......... A61B 50/10; A61B 50/20; A61B 50/30; A61B 90/60
USPC ............................................................ 606/1
See application file for complete search history.

(56) References Cited

U.S. PATENT DOCUMENTS

| 5,505,623 A * | 4/1996 | Chernack | G09B 23/30 434/270 |
| 5,971,763 A * | 10/1999 | Yau | G09B 19/00 132/319 |
| 6,637,411 B2 * | 10/2003 | Makiyama | F02M 61/14 123/456 |
| 6,830,037 B1 * | 12/2004 | Braun | F02M 63/0225 123/470 |
| 2002/0198514 A1 * | 12/2002 | Barzell | A61B 90/11 606/1 |
| 2004/0153031 A1 * | 8/2004 | Van Kaauwen | A61M 5/427 604/116 |
| 2009/0326400 A1 * | 12/2009 | Huldt | A61B 5/04085 600/509 |
| 2014/0039451 A1 * | 2/2014 | Bangera | B29C 64/393 604/506 |
| 2016/0242853 A1 * | 8/2016 | Bangera | A61M 5/427 |
| 2016/0257162 A1 * | 9/2016 | Cruickshank | B43L 1/00 |
| 2018/0117364 A1 * | 5/2018 | Jordan | A61N 7/00 |
| 2018/0261126 A1 * | 9/2018 | Rios | G09B 23/28 |
| 2019/0130792 A1 * | 5/2019 | Rios | A61M 5/46 |
| 2020/0093997 A1 * | 3/2020 | Jandali | A61M 5/427 |
| 2020/0146615 A1 * | 5/2020 | De Maio Domingos | G16H 50/20 |

* cited by examiner

*Primary Examiner* — Carl H Layno
*Assistant Examiner* — Michael J Lau
(74) *Attorney, Agent, or Firm* — Quarles & Brady LLP (57) ABSTRACT

A system for visual staging includes a staging board having a plurality of receptacles spaced apart from each other and extending into a thickness of the staging board, the staging board has an anatomical image that is viewable on a top surface of the staging board. A plurality of clips are configured to be received by and extend from the plurality of receptacles such that the clips are releasably connected to the staging board. The plurality of receptacles are spaced apart from each other at strategic positions on the staging board in relation to the anatomical image.

14 Claims, 13 Drawing Sheets

SYSTEMS AND METHODS FOR VISUAL STAGING OF MEDICAL DEVICES

CROSS REFERENCE TO RELATED APPLICATIONS

Not applicable.

BACKGROUND OF THE INVENTION

Medical procedures, including minimally invasive outpatient procedures, are typically preplanned. The level of planning can vary greatly depending on the invasiveness of the ultimate procedure, the time required to conduct the procedure, the medical and surgical tools required to complete the procedure, and the personnel needed to staff the procedure.

Planning of medical procedures can also be an important step in preserving a highly skilled medical practitioner's time in order to efficiently complete an increased number of procedures in a given day. One pervasive issue in the medical profession is the desire to effectively treat as many patients as possible in an efficient manner, while maintaining patient-specific goals.

In light of these challenges, a need exists for systems and methods for visual staging of medical devices.

SUMMARY OF THE INVENTION

Some embodiments of the disclosure provide a system for visual staging. The system for visual staging can include a staging board having a plurality of receptacles spaced apart from each other and extending into a thickness of the staging board. The staging board can have an anatomical image that is viewable on a top surface of the staging board. The system can also have a plurality of clips configured to be received by and extend from the plurality of receptacles such that the clips are removably connected to the staging board. The plurality of receptacles can be spaced apart from each other at strategic positions on the staging board in relation to the anatomical image. The staging board can have at least one spacer attached to a surface of the board, the at least one spacer can provide spacing between the staging board and a second staging board such that the staging board and the second staging board are stackable. The anatomical image can be of the anatomical structure of a human face. A first set of the plurality of receptacles can be arranged parallel with and along a longitudinal axis of the staging board and a second set of the plurality of receptacles are offset from and arranged at an angle with respect to the longitudinal axis of the staging board. The staging board can have a dry erase marker finish on the top surface of the staging board. The staging board can comprise a clear polycarbonate material. The plurality of clips can each have an upper portion and a lower portion. The upper portion of each clip comprises a U-shaped profile that is open from above the clip such that the upper portion of the clip is configured to receive the device in a central opening of the clip, and the lower portion of each clip comprises a central slot positioned between two legs, the two legs each having an upper ledge for contacting a bottom surface of the staging board. The plurality of receptacles can be openings formed through the thickness of the staging board. The plurality of clips can be interchangeable.

Other embodiments of the disclosure provide a method of assembling a system for visual staging. The method can include providing at least one staging board having a plurality of receptacles spaced apart from each other and extending into a thickness of the staging board, the staging board has an anatomical image that is viewable on a top surface of the staging board. The method can also include providing a plurality of clips configured to be received by and extend from the plurality of receptacles such that the clips are secured to the staging board. The plurality of receptacles can be spaced apart from each other at strategic positions on the staging board in relation to the anatomical image. The method can include manufacturing the staging board using a laser cutting technique or an injection molding technique. The method can include attaching at least one spacer to a surface of the staging board. The method can also include providing a second staging board and stacking the second staging board with the staging board where the at least one spacer provides spacing between the staging board and the second staging board.

Other embodiments of the disclosure provide a system for visual staging. The system can include a staging board having a plurality of securing devices spaced apart from each other at positions correlated to anatomical features depicted on an anatomical image that is viewable on a top surface of the staging board, the securing devices can extend away from the top surface of the staging board and are configured to releasably secure treatment devices.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Given the benefit of this disclosure, various modifications to the illustrated embodiments will be readily apparent to those skilled in the art, and the underlying principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIGS. 1A-3 illustrate a visual staging system 30 according to an embodiment of the disclosure. The visual staging system 30 has a staging board 32 that has a plurality of receptacles 34 spaced apart from each other and extending into a thickness of the staging board 32. In some embodiments, the staging board 32 has an anatomical image (e.g., see a non-limiting example depicted in FIG. 16) that is viewable on a top surface of the staging board 32. The staging board 32 can take any appropriate shape, such as rectangular, square, circular, oval, triangular, hexagonal, or any other appropriate shape (e.g., a form factor corresponding to the anatomical image supported thereon, such as the form of a right hand having a wrist, palm, and fingers/ thumb). As illustrated, the staging board 32 has a rectangular shape with rounded corners and is generally planar, but may be convex, concave, undulating, or any other non-planar form factor. The staging board 32 can comprise a number of appropriate materials, some non-limiting examples can be polyoxymethylene, acrylonitrile butadiene styrene, polycarbonate, polyethylene, polypropylene, and metals (such as stainless steel, aluminum, etc.). For example, the staging board 32 can comprise a clear polycarbonate material, the clear polycarbonate material can have a re-useable finish (e.g., a dry erase marker finish) on the top surface 36 of the staging board 32.

With additional reference to FIGS. 7A-7D, in the example embodiment using receptacles 34, the receptacles 34 are shown spaced apart from each other at strategic positions on the staging board 32, the strategic positions may be in relation to an anatomical image on the staging board 32. A first set 38 of the plurality of receptacles 34 are arranged parallel with and along a longitudinal axis 40 of the staging board 32. A second set 42 of the plurality of receptacles 34 are offset from and arranged laterally with respect to the longitudinal axis of the staging board and oriented at an angle (i.e., skewed) relative to the orientation of the first set 38. In some embodiments, the second set 42 of the plurality of receptacles 34 can be mirrored across the longitudinal axis 40 of the staging board 32. A third set 44 of the plurality of receptacles 34 can be offset further from the longitudinal axis 40 than the second set 42 and can be mirrored across the longitudinal axis 40 of the staging board 32.

Figure 7A:
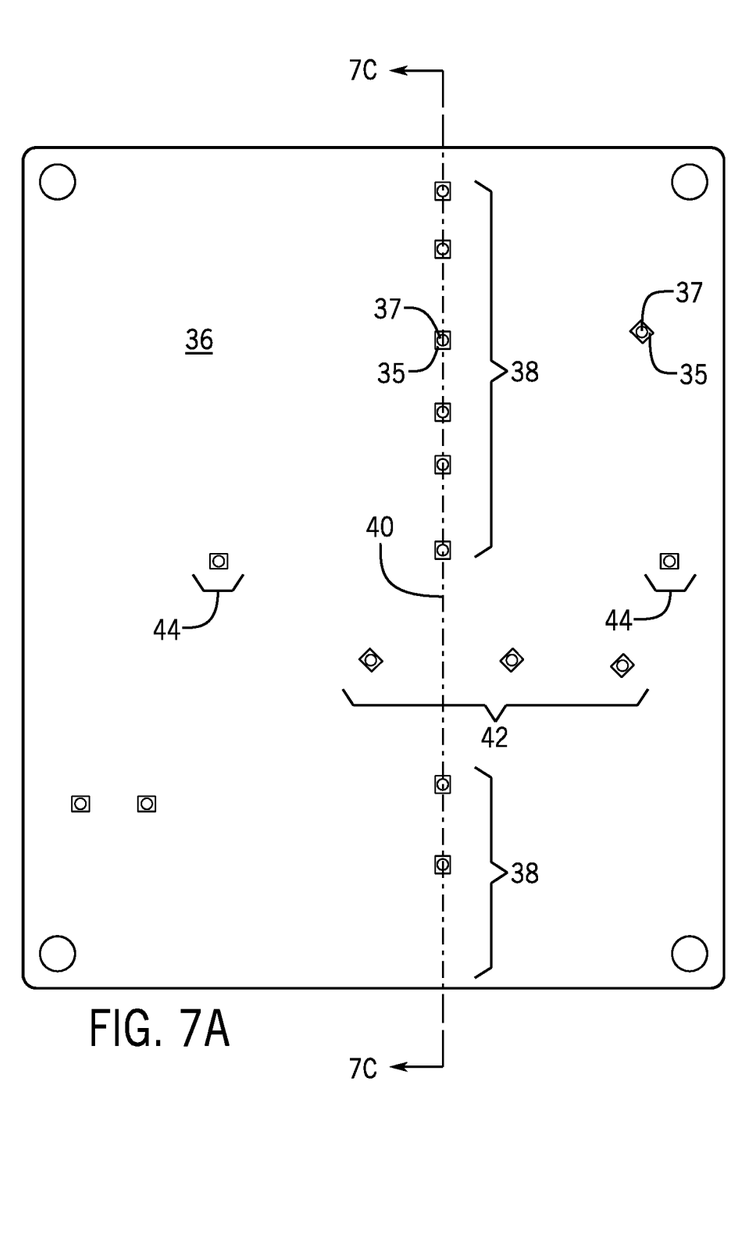
FIG. 7A is a top plan view of the staging board of FIG. 1A.
Figure 7B:
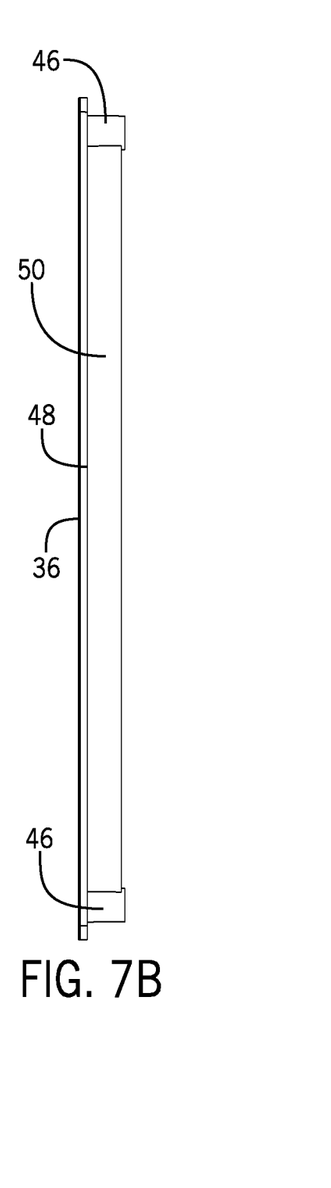
FIG. 7B is a side plan view of the staging board of FIG. 7A.
Figure 7C:
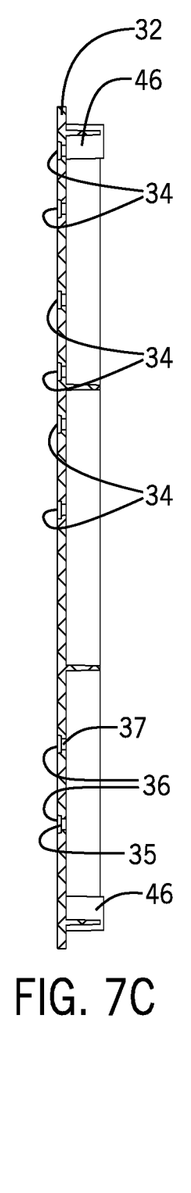
FIG. 7C is a cross-sectional view of the staging board along line 7C-7C of FIG. 7A.
Figure 7D:
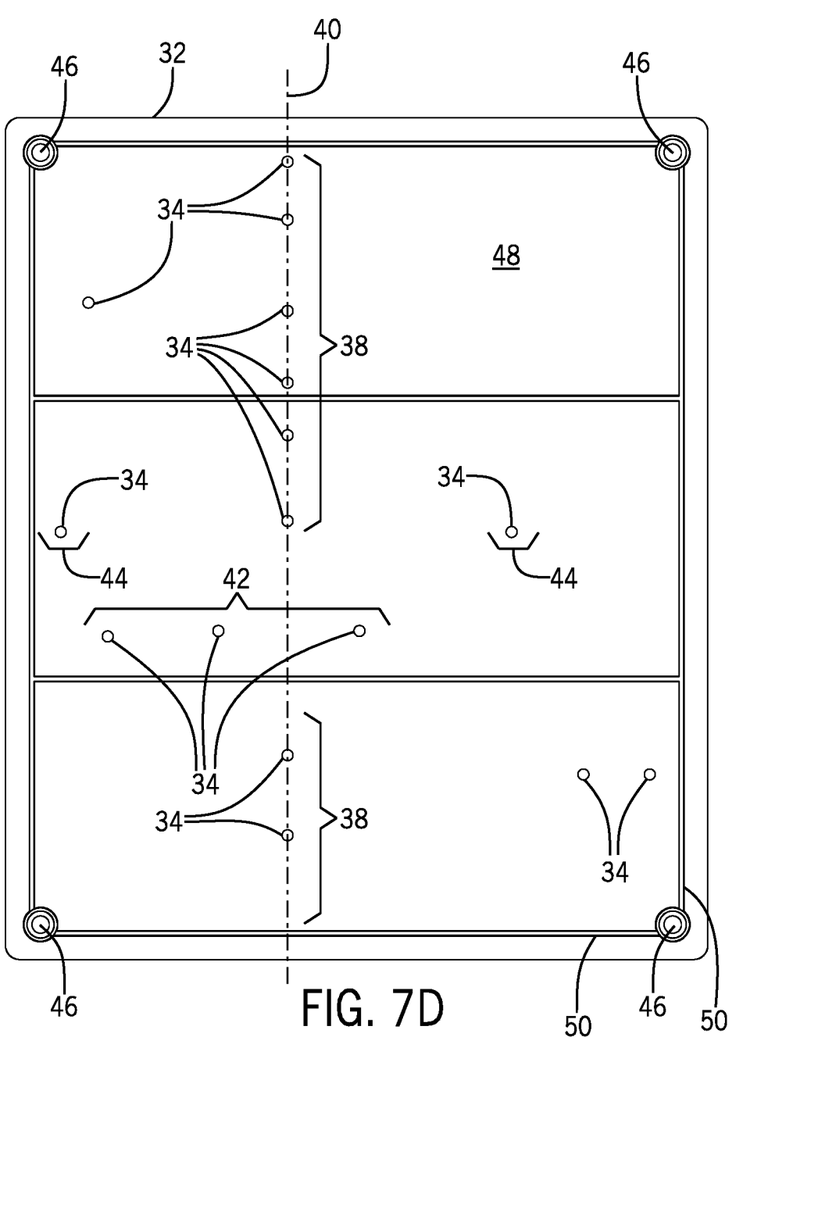
FIG. 7D is a bottom plan view of the staging board of FIG. 7A.
Figure 8A:
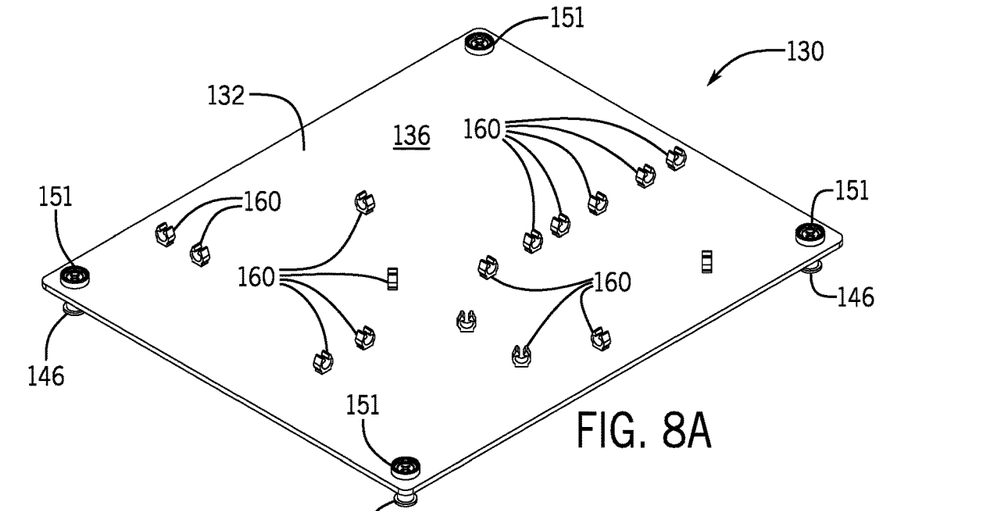
FIG. 8A is an isometric view of a visual staging system according to another embodiment of the disclosure.
Figure 8B:
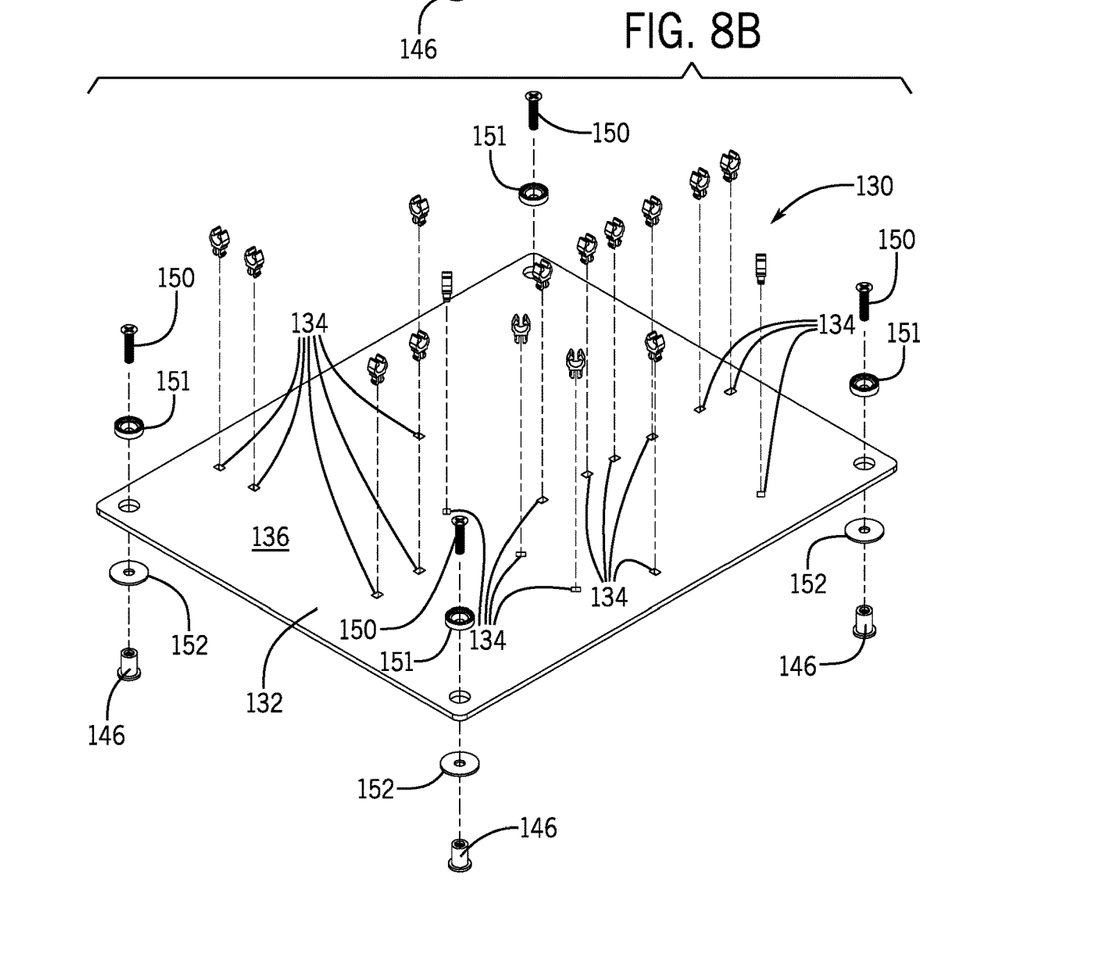
FIG. 8B is an isometric exploded view of the visual staging system of FIG. 8A.
Figure 9:
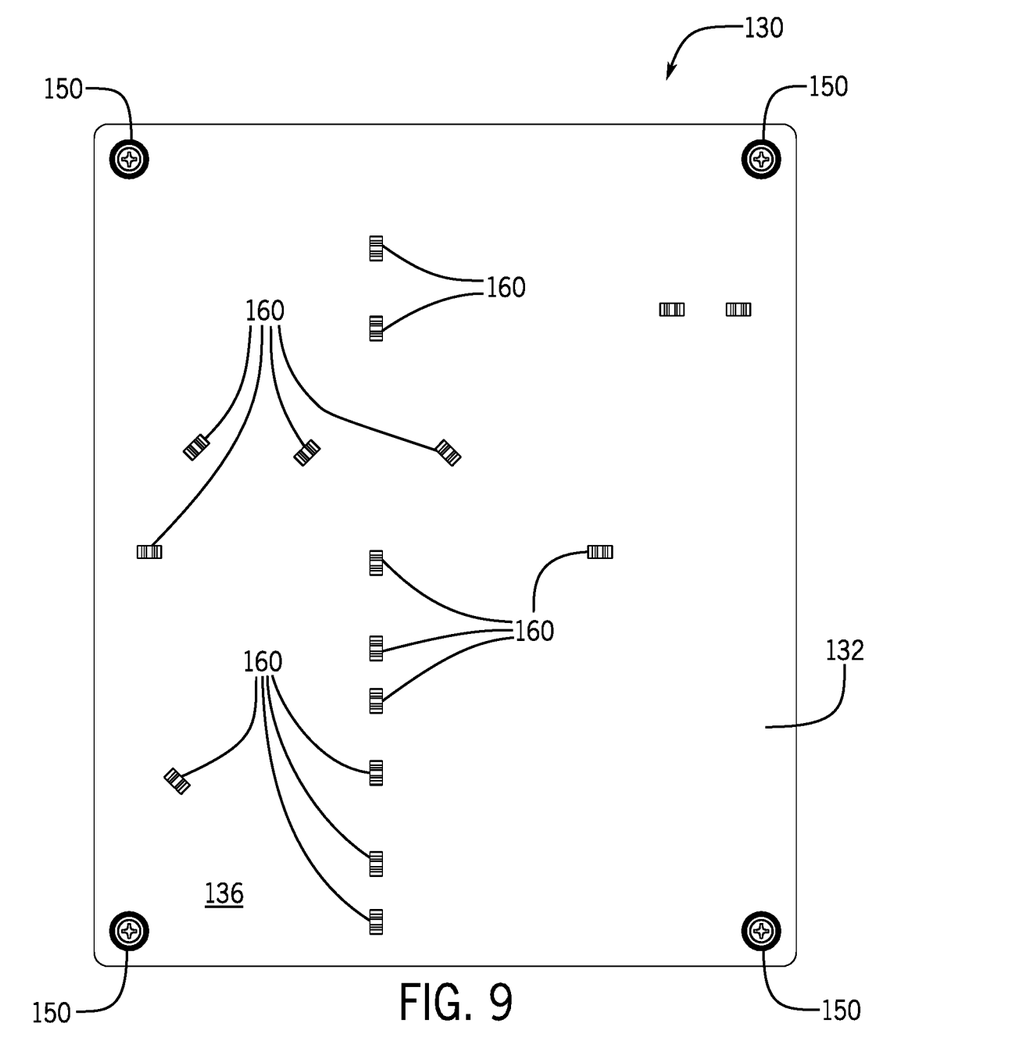
FIG. 9 is a top plan view of the visual staging system of FIG. 8A.
Figure 10:
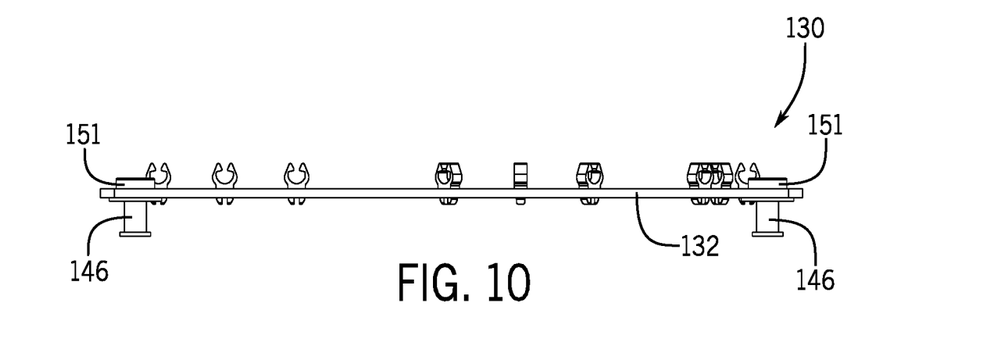
FIG. 10 is a side plan of the visual staging system of FIG. 8A.
Figure 11A:
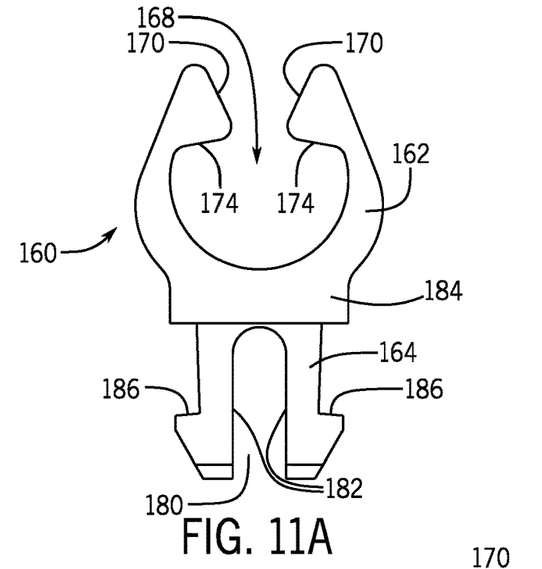
FIG. 11A is a front plan view of a clip according to another embodiment of the disclosure.
Figure 11B:
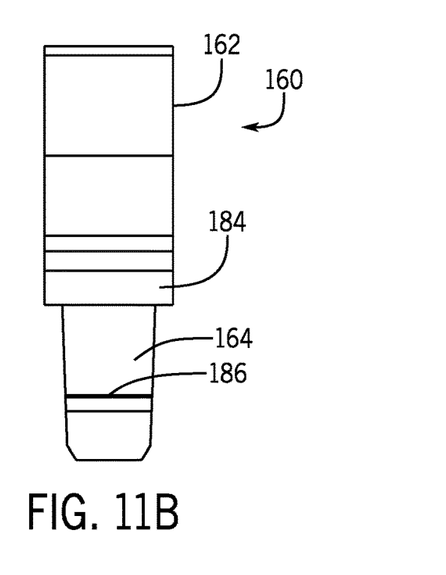
FIG. 11B is a side plan view of the clip of FIG. 11A.
Figure 12:
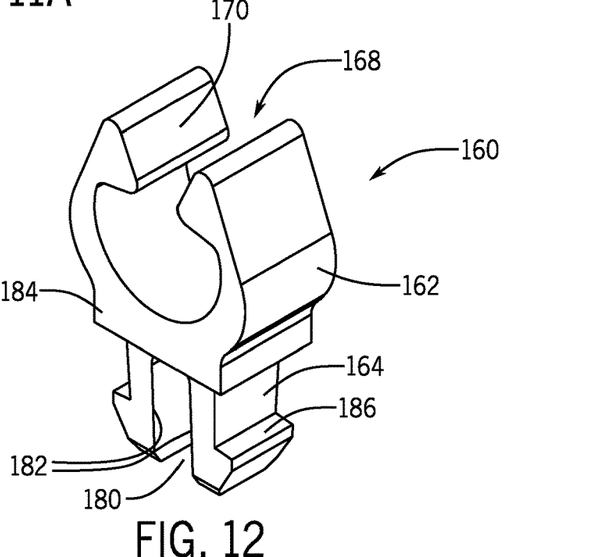
FIG. 12 is an isometric view of the clip of FIG. 11A.
Figure 13A:
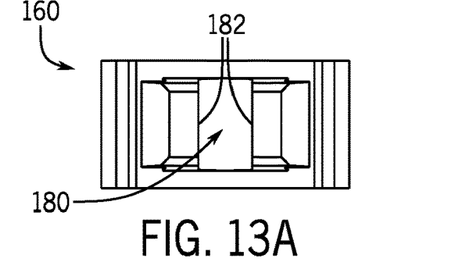
FIG. 13A is a bottom plan view of the clip of FIG. 11A.
Figure 13B:
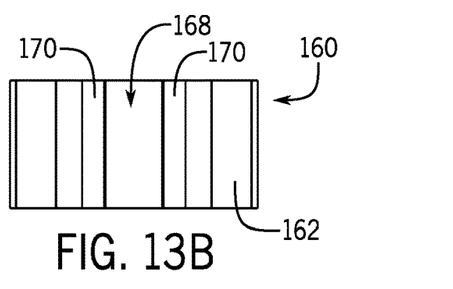
FIG. 13B is a top plan view of the clip of FIG. 11A.
Figure 14A:
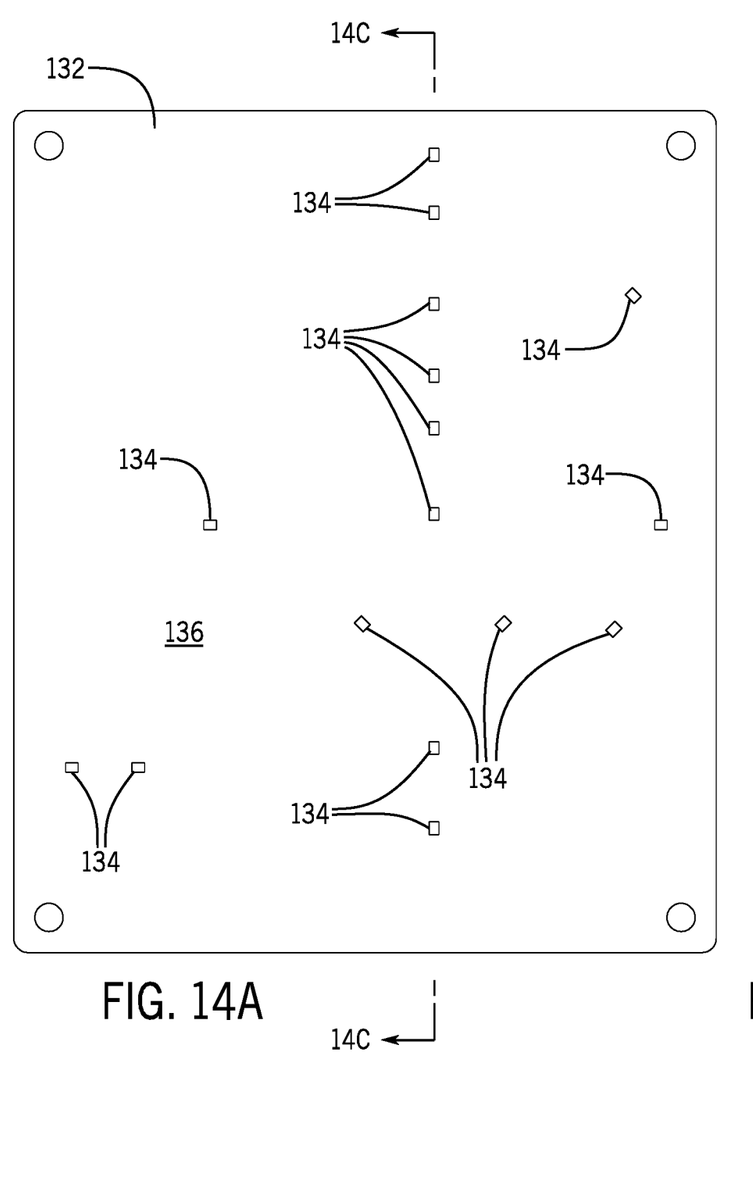
FIG. 14A is a top plan view of the staging board of FIG. 8A.
Figure 14B:
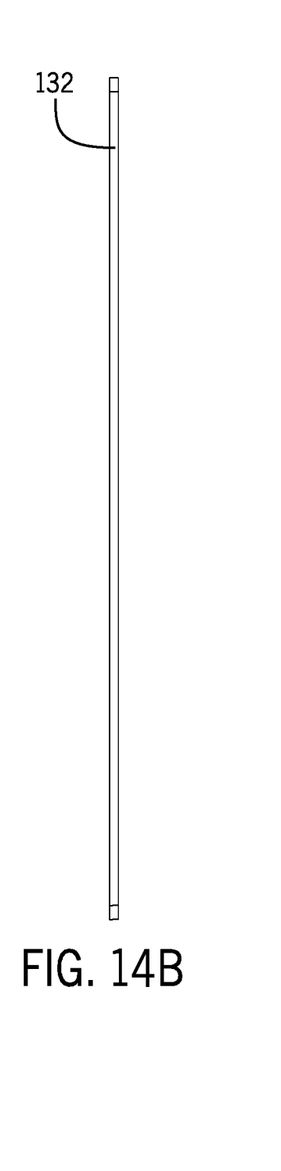
FIG. 14B is a side plan view of the staging board of FIG. 14A.
Figure 14C:
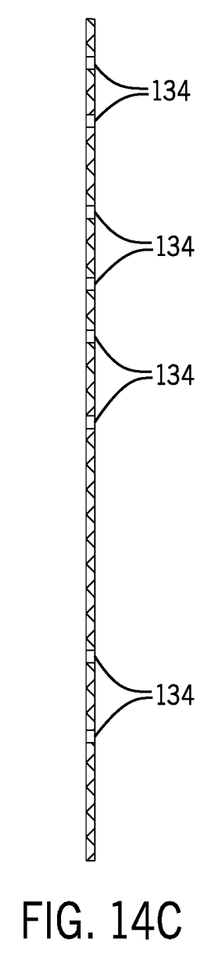
FIG. 14C is a cross-sectional view of the staging board along line 14C-14C of FIG. 14A.
Figure 14D:
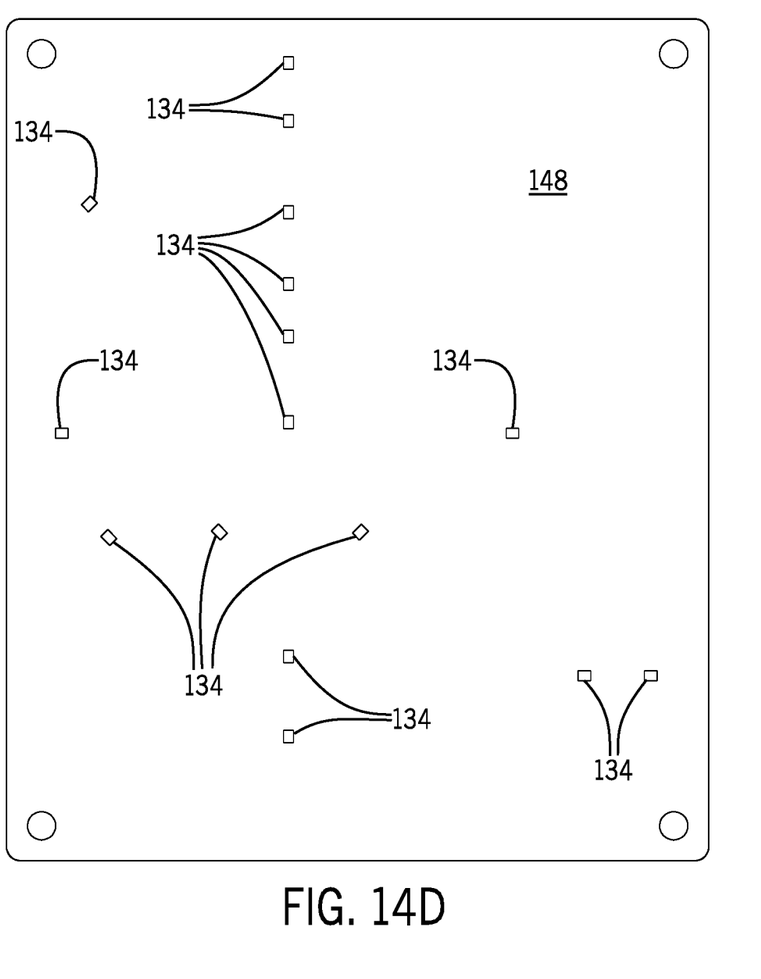
FIG. 14D is a bottom plan view of the staging board of FIG. 14A.

The receptacles 34 can be any number and orientation of receptacles such as openings that extend through the thickness of the staging board 32 or cavities that extend into the thickness of the board 32 and not through the entire thickness of the board 32. As best illustrated in FIGS. 7A, 7C, and 7D, the example receptacles 34 define a generally rectangular upper portion 35 extending part way through the thickness of the board 32 and an adjacent generally cylindrical lower portion 37 that extends through the remainder of the board 32. Additionally, the receptacles 34 can accommodate securing devices (discussed below) engaged with the staging board 32 via a variety of securing means such as mechanical fasteners (e.g., screws, nails, pins, bolts, etc.), magnetism, welding, sonic welding, adhesives, or any other suitable securing means that adequately restrains the securing devices to the staging board 32 during use.

The staging board 32 additionally has at least one spacer 46 attached to (or integral with) the staging board 32. The spacer 46 can extend from a bottom surface 48 of the staging board 32 to provide spacing between the staging board 32 and a second staging board having a similar basic construction of the staging board 32 such that the staging board and the second staging board are stackable (e.g., see FIG. 15 for an exemplary illustration). As shown, the staging board 32 has four (4) spacers 46 positioned near each corner of the staging board 32 with caps 47 (shown removed in FIG. 1B) attached to the bottom of each spacer 46. A ledge 50 can extend between the spacers 46 below the bottom surface 48 of the staging board 32. The ledge 50 can be offset from the exterior perimeter of the staging board 32. Any arrangement of spacers 46 can be utilized, for example, spacers 46 could be placed at opposing corners across the staging board 32.

Figures 18, 19:
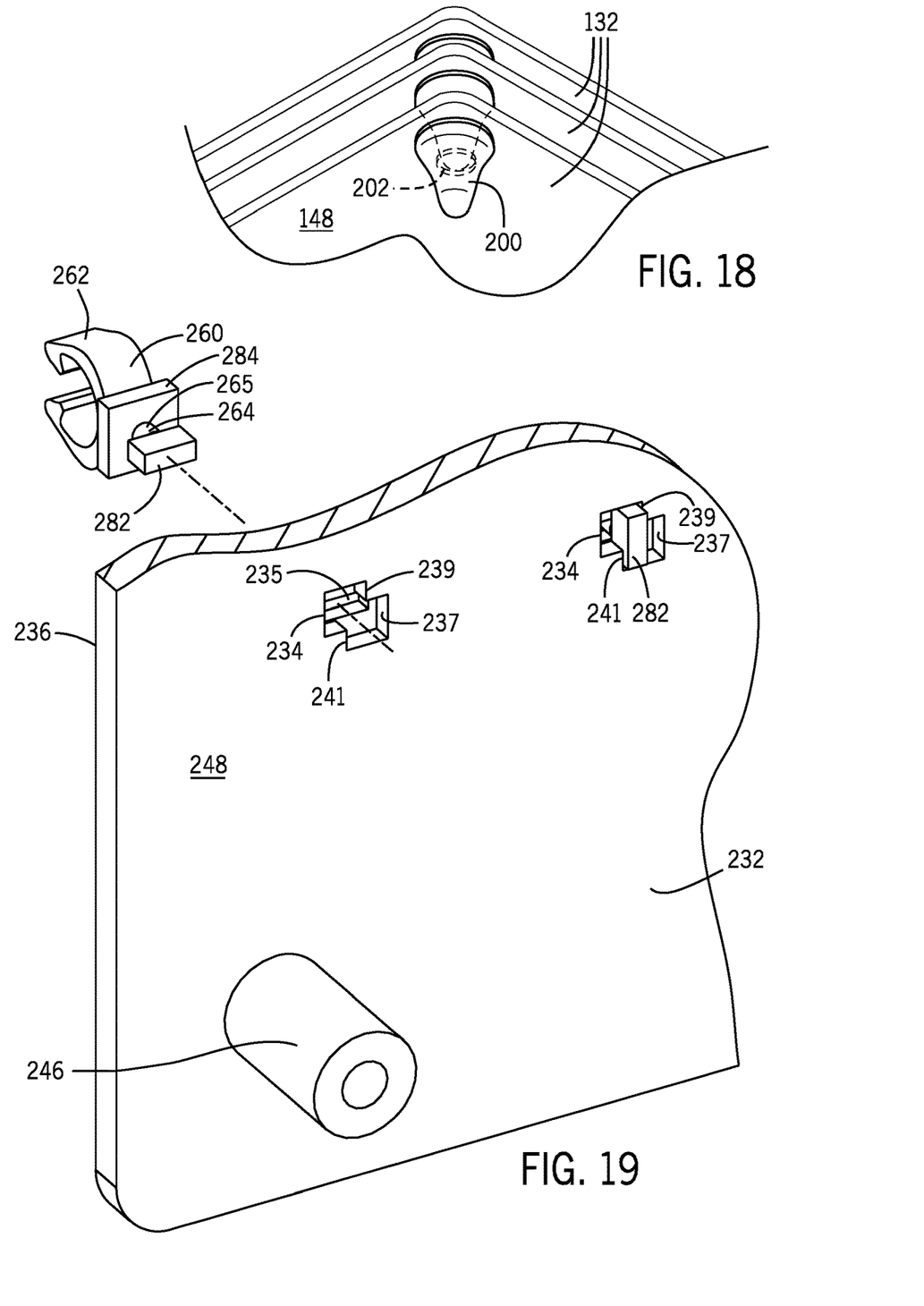
FIG. 18 is a partial isometric view of three (3) stacked visual staging systems according to another embodiment of the disclosure.
FIG. 19 is a perspective view of a portion of a visual staging system according to another embodiment of the disclosure.

A single spacer 46 could be utilized as well and could be centrally positioned on the staging board 32. The spacer 46 can also have a variety of form factors, such as cylindrical, flared, conical, and the like. In a non-limiting embodiment, the spacer 46 can be a conical standoff 200 connected to and extending from the bottom surface 148 of the staging board 132, as shown in FIG. 18. The conical standoff 200 can be connected to the staging board 132 via an adhesive.

Securing device, such as a plurality of example clips 60, are configured to be received by and extend from the plurality of receptacles 34 such that the clips 60 are releasably connected to the staging board 32 via the receptacles 34. As used herein, "releasably connected" refers to the ability for the clips 60 to be connected to the staging board 32 such that they are secured to the board in a non-permanent manner. Accordingly, the clips 60 can be removed or interchanged as needed, for example if a clip 60 is broken or to accommodate a different device. As shown in FIGS. 4A-6B the plurality of clips 60 each have an upper portion 62 and a lower portion 64. The upper portion 62 of each clip 60 comprises a U-shaped profile that is open from above the clip 60 such that the upper portion 62 of the clip can receive a device (discussed below) in a central opening 68 of the clip 60. The central opening 68 can be accessed between two angled edges 70 at the upper end 72 of the clip 60. The angled edges 70 transition into upper lips 74 that transition the angled edges 70 back into the U-shape of the upper portion 62.

Figure 1A:
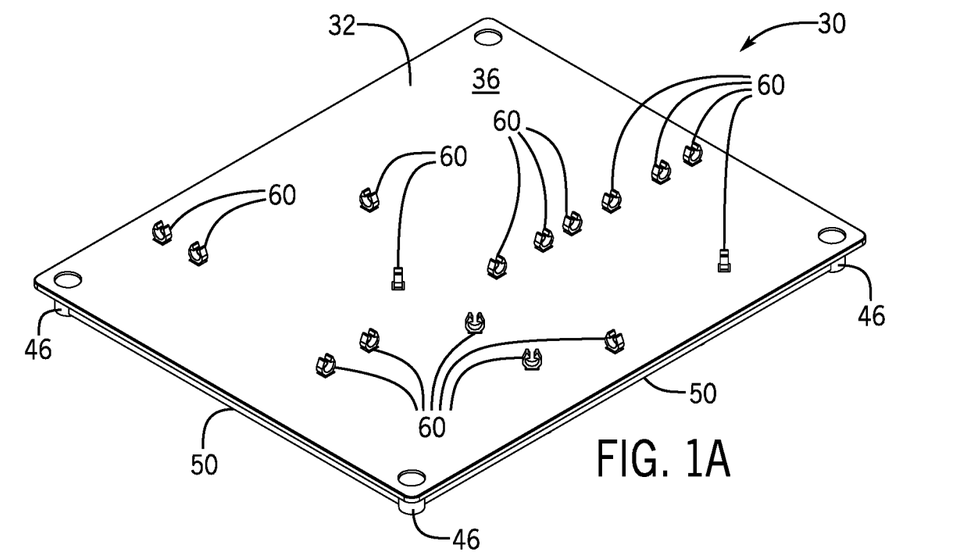
FIG. 1A is an isometric view of a visual staging system according to one embodiment of the disclosure.
Figure 1B:
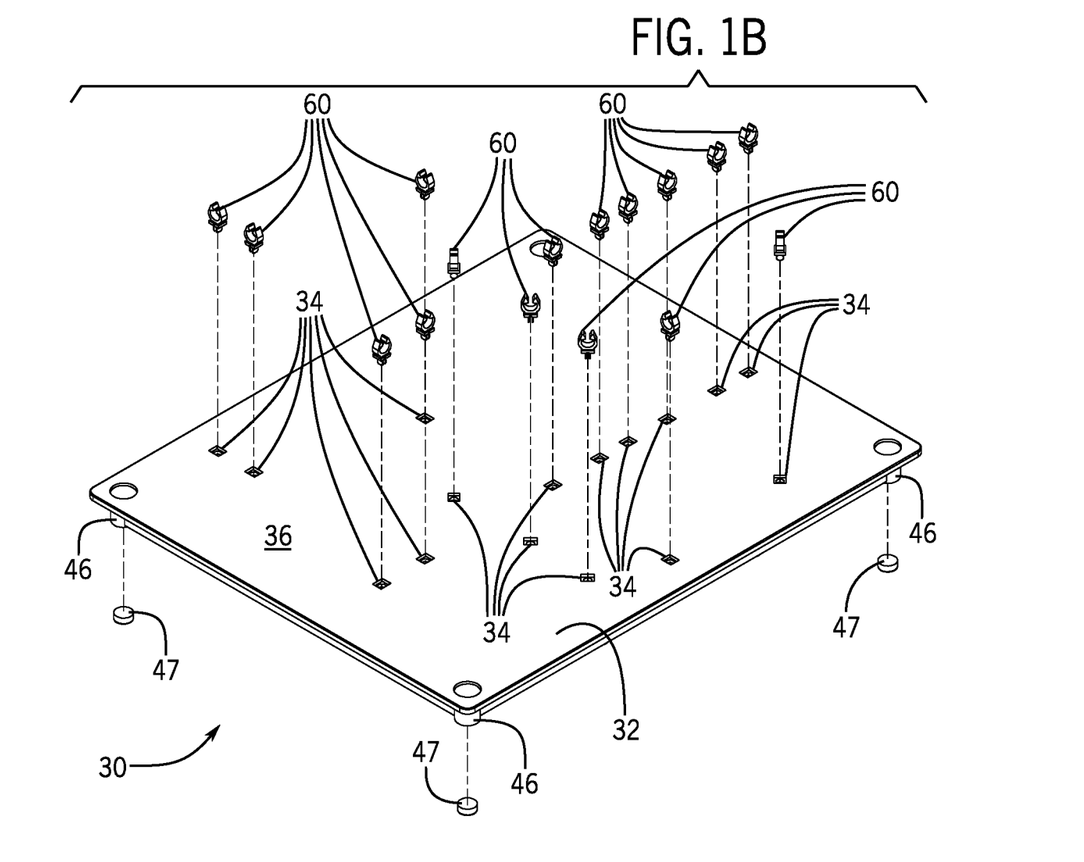
FIG. 1B is an isometric exploded view of the visual staging system of FIG. 1A.
Figure 2:
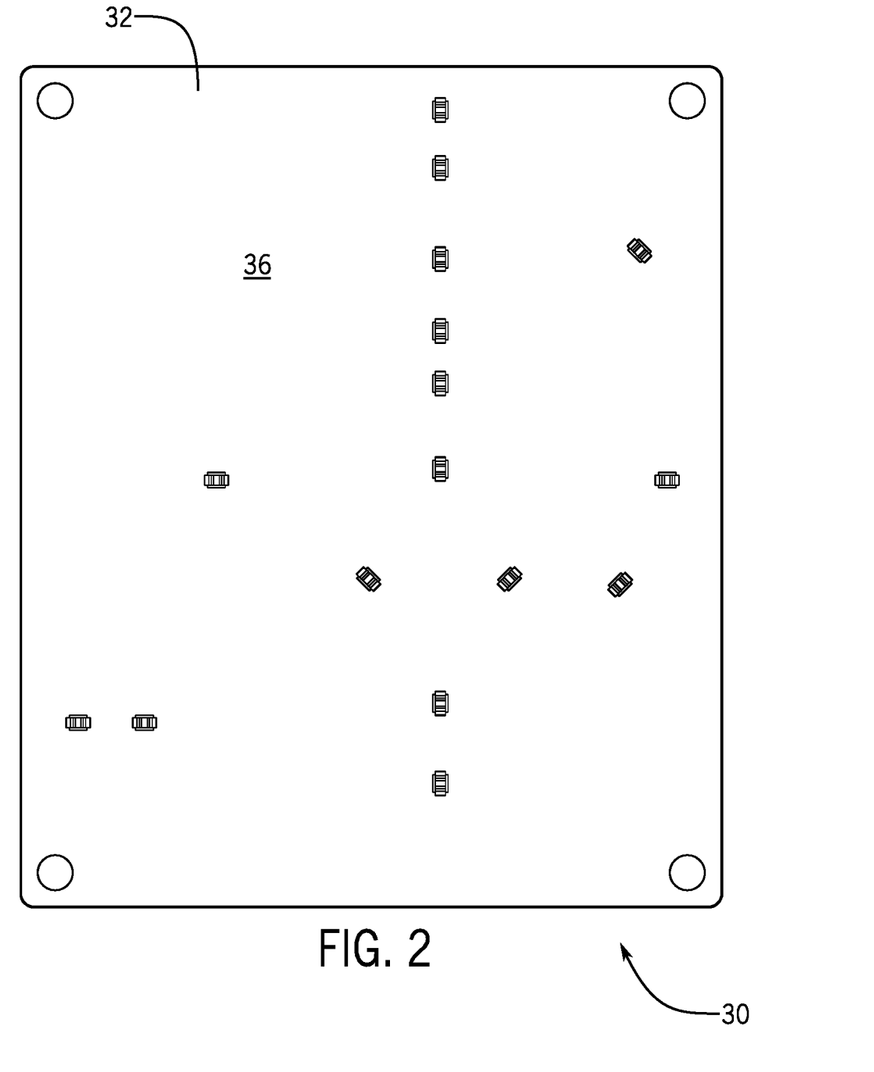
FIG. 2 is a top plan view of the visual staging system of FIG. 1A.
Figure 3:
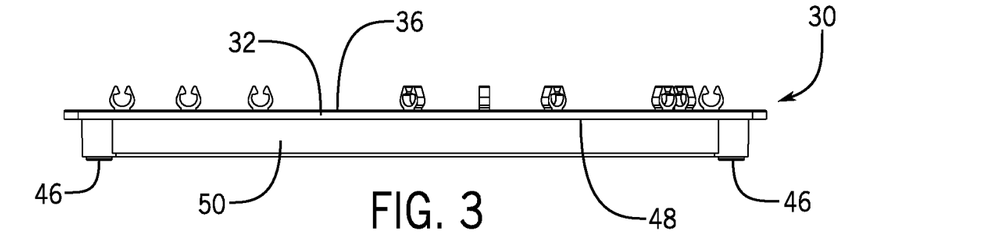
FIG. 3 is a side plan of the visual staging system of FIG. 1A.
Figure 4A:
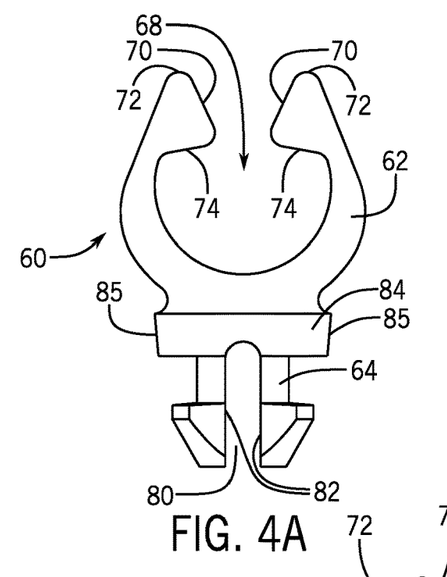
FIG. 4A is a front plan view of a clip according to an embodiment of the disclosure.
Figure 4B:
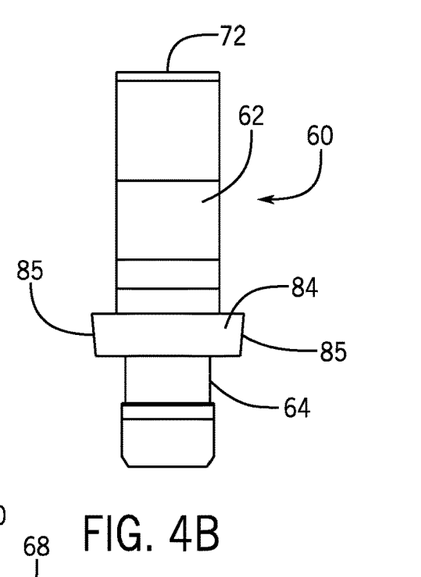
FIG. 4B is a side plan view of the clip of FIG. 4A.
Figure 5:
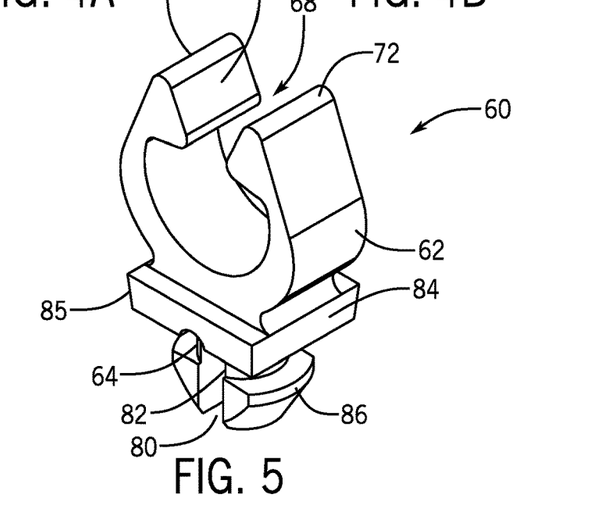
FIG. 5 is an isometric view of the clip of FIG. 4A.
Figure 6A:
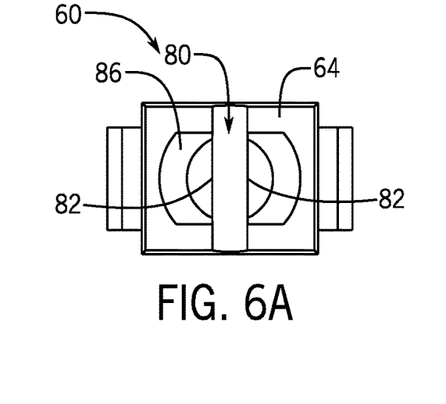
FIG. 6A is a bottom plan view of the clip of FIG. 4A.
Figure 6B:
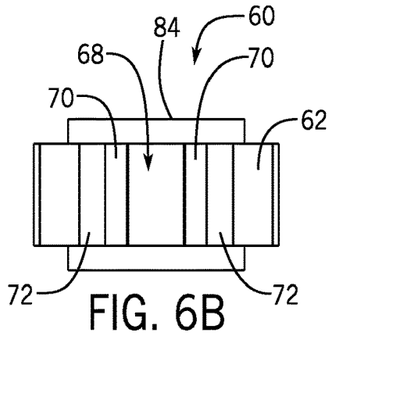
FIG. 6B is a top plan view of the clip of FIG. 4A.

A base 84 of the upper portion 62 extends outwardly from the upper portion 62 and connects the upper portion 62 to the lower portion 64. The lower portion 64 of each clip 60 has a central slot 80 positioned between two opposing legs 82. The two legs 82 each have an upper ledge 86 that, when inserted into an exemplary opening such as a receptacle 34, contact the bottom surface 48 of the staging board 32. Each ledge 86 is the result of an outward radial projection of the two legs 82. The clips 60 can comprise a number of appropriate materials, some non-limiting examples can be polyoxymethylene, acrylonitrile butadiene styrene, polycarbonate, polyethylene, polypropylene, and metals (such as stainless steel, aluminum, etc.). The legs 82 deform axially inward when urged into the respective receptacle 34, closing a space of the central slot 80 between the legs 82. When the upper ledge 86 clears the bottom surface 48 of the staging board 32, the legs 82 resiliently spring outward to a nominal orientation (e.g., as shown in FIG. 4A). The base 84 of each clip 60 is also contoured to seat within a mating form factor defined by the receptacle 34. In the example shown, the base 84 is generally rectangular with side surfaces 85 that tapper inward and downward at an angle to generally match mating beveled surfaces defined by the receptacle 34. The interaction between the mating beveled surfaces aids in the secure placement and restraint of the clips 60 relative to the board 32. A variety of form factors can be used to aid securement of the clips 60 to the board 32 (e.g., conical).

The example clips 60 can be secured to the staging board 32 via the receptacles 34. The clips 60 can receive devices at the strategic positions. As used herein, the term "devices" is used to refer to any number of appropriate devices for use with the visual staging system. Devices can include, but are not limited to, the following: syringes, needles, pens, markers, medication containers, cutting tools (e.g., scalpels, drills, shears, etc.), awls, chisels, curettes, gouges, mallets, pliers, osteotomes, rasps, rongeurs, wire and pin instruments, electrosurgical instruments such as bipolar and monopolar forceps, cables, electrosurgical units, cannulas, calipers, gauges, markers, rulers, clamps, forceps, graspers, elevators, spreaders, dissectors, elevators, hooks, probes, endo brow lift instruments, knives, punches, needle holders, speculums and retractors in styles such as hand-held or self-retaining or fiberoptic, and scissors, among others.

Each of the example receptacles 34 is configured to engage a securing device (e.g., a clip 60) via a securing means (e.g., a biased mechanical engagement described below). In other forms, the securing device can be, for instance, integral with the board 32 (such that receptacle structures are not present) or semi-permanently secured to the board 32 (e.g., adhered, coupled via a sonic welding process). Securing devices can include a variety of structures that engage the receptacles 34 (or are directly/integrally formed with the board 32) and establish removable coupling between the securing device and an application-specific device. Accordingly, the form of the securing device (e.g., the example clip 60) can be adapted to accommodate the device of a particular application. The clip 60, for instance, can include an upper portion 62 with fewer or more structures of arcuate or discrete form factors that interact to releasable restrain the device during use. In one example, the securing device can comprise a U-shaped saddle with an arm hinged to one of the upper ends of the saddle. The arm can be pivoted between an opened position, whereat a device can be received in the saddle, and a closed position whereat a resilient distal end of the arm can be releasably engaged with a locking tab that extends outward from the other end of the saddle to restrain the device within the saddle. In a further embodiment, the securing device may include a spring loaded clamp (e.g., a circular ring) that can be urged from a natural engaged position, at which a device is secured by the securing device, to a disengaged position, at which the device can be moved relative to the securing device. Given the benefit of this disclosure, various other constructions and arrangements of securing devices are within the purview of one of ordinary skill in the art.

In a non-limiting example, the clips 60 can hold syringes, which may be 5 mm and 6 mm syringes. The clips 60 can be removed if damaged or are not relevant for a particular procedure, and secure enough to withstand devices being placed in and pulled out of them during use of the visual staging system. The clips 60 can be flexible such that when a device is inserted via the central opening 68, contact between the device and the angled edges 70 can cause the upper portion 62 to flex to allow the device to be received into the central opening 68. Once received in the central opening 68, the upper lips 74 can retain the device within the clip 60 until the device is forcibly removed.

Figure 15:
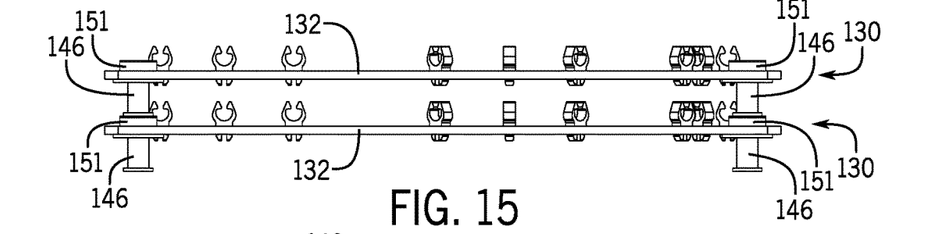
FIG. 15 is a side plan of two (2) stacked visual staging systems of FIG. 8A.

FIGS. 8A-15 illustrate a visual staging system 130 according to another embodiment of the disclosure. The visual staging system 130 shares many features with the visual staging system 30 described above. The visual staging system 130 has a staging board 132 that has a plurality of receptacles 134 arranged in a similar manner to the staging board 132 and the receptacles 34. At least one spacer 146 can be utilized in the visual staging system 130. The at least one spacer 146 can serve a similar purpose as the at least one spacer 46. As shown, four (4) spacers 146 are positioned near each of the four corners of the staging board 132. The spacers 146 are secured to the staging board 132 using fasteners 150 that extend through the staging board 132, each fastener 150 extends through a collar 151 that is cylindrical in shape and extends around the fastener 150. The collar 151 is positioned on or above a top surface 136 of the staging board 132. The fastener 150 also extends through a washer 152 and is received in a central bore of the spacer 146, which can be threaded, barbed, keyed, etc. in order to secure the fastener 150 to the spacer 146. As shown in FIG. 15, the staging boards 132 are stackable using the spacers 146 that provide sufficient clearance between the staging boards 132 and the clips 160 when the staging boards 132 are stacked, and can be configured to accommodate stacking of staging boards 132 while devices are engaged with the clips 160. The spacers 146 can be stacked with the base of the spacer 146 being received in or contacting the collar 151 of the other staging board 132.

There are some similarities and differences between the example clips 60 and the example clips 160. As illustrated in FIGS. 11A-13B, the upper portion 162 of the clips 160 has a similar structure as the upper portion 62 of the clips 60 including the central opening 168, the angled edges 170, the upper lips 174, and being substantially U-shaped. A base 184 of the upper portion 162 is flush with the upper portion 162 and connects the upper portion 162 to the lower portion 164. The lower portion 164, similarly, has a central slot 180 positioned between two legs 182. The lower portion 164 differs in ways from the lower portion 64. The two legs 182 each have an upper ledge 186 that, when inserted into an exemplary opening as a receptacle 134, contact the bottom surface 148 of the staging board 132. Each ledge 186 is the result of an outward projection of the two legs 182 that slightly tapper inward in a direction moving away from the base 184 (shown in FIG. 11B). The receptacle 134 may extend straight through the staging board 132 (i.e., not skewed or angled to the top surface 136 and the bottom surface 148). Again, the clips 160 can comprise a number of appropriate materials, some non-limiting examples can be polyoxymethylene, acrylonitrile butadiene styrene, polycarbonate, polyethylene, polypropylene, and metals (such as stainless steel, aluminum, etc.). The receptacles 134 generally define four walls that extend orthogonally between the top surface 136 and the bottom surface 148. The generally squared-off form factor of the receptacles 134 cooperates with the form factor of the clips 160 to securely receive the clips 160 during use.

Figure 16:
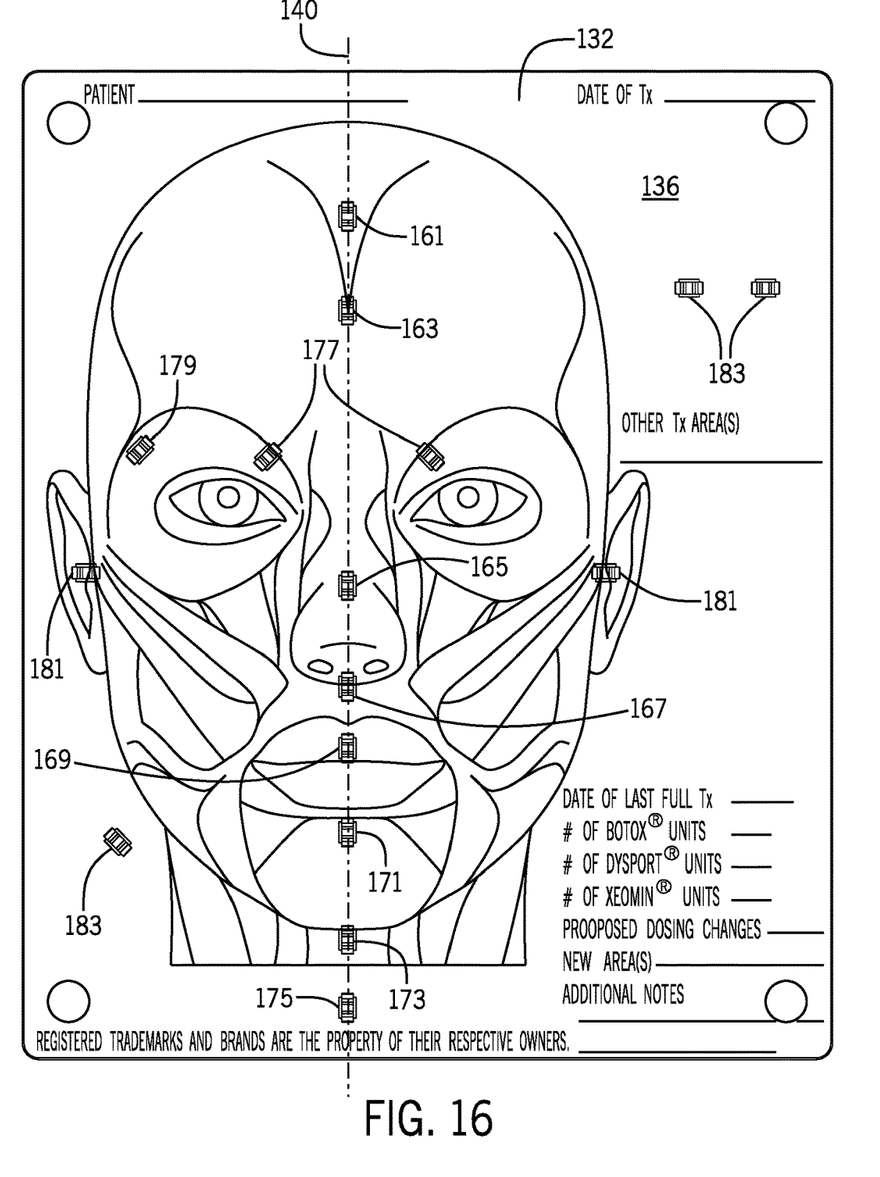
FIG. 16 is a top plan view of a visual staging system with an anatomical image according to another embodiment of the disclosure.

FIG. 16 illustrates an exemplary anatomical image placed (e.g., printed, adhered, etched, embedded, etc.) on the staging board 132. It is to be appreciated that an anatomical image, such as the one shown in FIG. 16, could also be placed on the staging board 32 and all description regarding the anatomical image is equally applicable to the visual staging system 30 and the visual staging system 130. Although the anatomical image illustrated is of a human face and the underlying tissues/features, any anatomical image could be used. Some non-limiting examples include: ears, noses, hands, feet, necks, shoulders, chests, abdomens, pelvic regions, legs, hairlines, and other areas.

As shown, the receptacles 134 position the clips 160 in strategic positions on the anatomical image to correlate the clips 160 to underlying anatomical features and structures of interest for a particular application. The first set 138 of the plurality of receptacles 134 are arranged parallel with and along a longitudinal axis 140 of the staging board 132 thereby positioning clips 160 at each respective location, which corresponds to a longitudinal axis of the human face in the anatomical image. The first set 138 of receptacles 134 places two clips on the longitudinal axis 140 near the top of the human face, a first clip 161 at or above a hairline and a second clip 163 at the base of a hairline or positioned on the forehead of the face. The first set 138 continues downwardly along the longitudinal axis 140 and places a third clip 165 on the nasal ridge of the face, a fourth clip 167 at or near the columella, a fifth clip 169 on the upper lip, a sixth clip 171 near the superior portion of the mentalis, a seventh clip 173 near the inferior portion of the mentalis, and an eighth clip 175 inferior to the seventh clip 173.

A second set 142 of the plurality of receptacles 134 are offset from and arranged at an angle with respect to the longitudinal axis 140 of the staging board 132 to arrange a number of clips 160 in strategic locations on the anatomical image. The second set 142 can include corrugator clips 177 positioned at medial positions corresponding to the corrugator muscles of the face at mirrored angles across the longitudinal axis 140. Secondary corrugator clips 179 can be positioned laterally from the corrugator clips 177 and can be similarly mirrored across the longitudinal axis 140. Ear clips 181 can be positioned at each ear of the image, and additional clips 183 can be positioned at other areas on the staging board 132 to provide staging for other treatment areas. In some embodiments, the second set 142 of the plurality of receptacles 34 can be mirrored across the longitudinal axis 140 of the staging board 132.

Each of the clips 160, as described above, can serve as securing device for any one of the devices described above. As an example regarding FIG. 16, the clips 160 (and clips 161 through 183) can receive a syringe that was prepared with a specific amount of fluid for each desired treatment area. This fluid could take any appropriate form, some non-limiting examples of which can be: water, saline, medication, onabotulinumtoxinA (BOTOX®), abobotulinumtoxinA (DYSPORT®) material, incobotulinumtoxinA (XEOMIN®) material, gels, hyaluronic gels, dermal fillers, cosmetic medications, anesthetics, pain relief medication, moisturizers, hygienic medications/materials, among others. The fluid can be prepared in the proper amount and/or dosage to be administered to the subject of the planned procedure.

The staging board 132 can have a re-useable surface property (e.g., surface configured for dry or wet erase markers) such that notes can be made on the board. Some examples can be seen in FIG. 16 where other treatment areas can be notes as well as the patient name, date of treatment, date of last treatment, number of BOTOX® units, number of DYSPORT® units, number of XEOMIN® units, proposed dosing changes, new areas, and additional notes.

A method of assembling a system for visual staging is also provided in this disclosure. The method may comprise providing at least one staging board (such as the staging board 32, 132) having a plurality of receptacles (such as receptacles 34, 134) spaced apart from each other and extending into a thickness of the staging board, the staging board has an anatomical image that is viewable on a top surface of the staging board. The method may also comprise providing a plurality of clips (such as clips 60, 160) configured to be received by and extend from the plurality of receptacles such that the clips are secured to the staging board. The plurality of openings are spaced apart from each other at strategic positions on the staging board in correlated relation to the anatomical image.

In some embodiments, the method can comprise manufacturing the staging board and the clips using a laser cutting technique. In another embodiment, the method can comprise manufacturing the staging board and the clips using an injection molding technique. The staging board can have at least one spacer attached to a surface of the board. The method may further comprise providing a second staging board and stacking the second staging board with the staging board where the at least one spacer provides spacing between the staging board and the second staging board.

Figure 17:
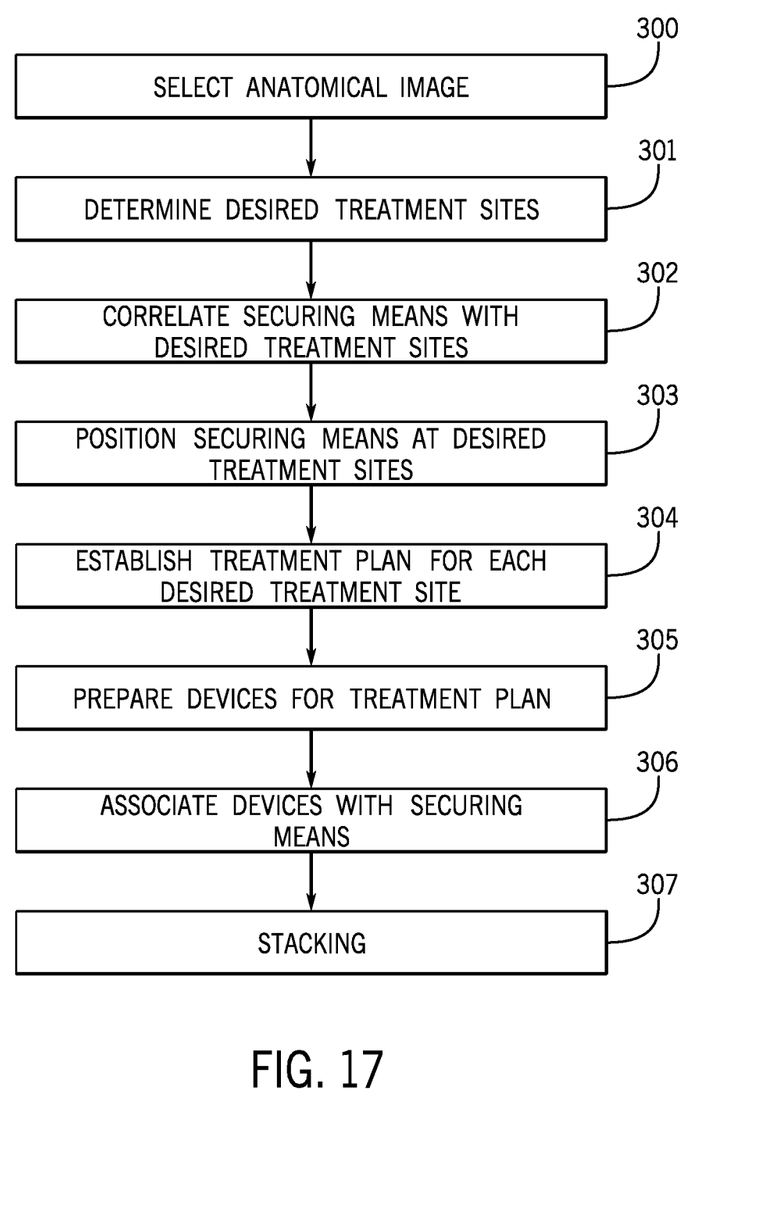
FIG. 17 is a flow chart of a method of visual staging according to an embodiment of the disclosure.

FIG. 17 illustrates a method of visual staging according to another embodiment of the disclosure. The method of visual staging can include selecting an anatomical image at process block 300 for the visual staging method to be applied. After selecting an anatomical image, determining desired treatment sites 301 based on the anatomical image, and correlating securing devices with the desired treatment sites 302 may occur. Next, positioning securing devices at desired treatment sites 303 may occur. The positioning devices can be any positioning devices described above. This may be followed by establishing a treatment plan for each desired treatment site 304, the treatment plan may be a medical treatment plan such as a cosmetic procedure treatment plan. The method can also include preparing devices for the treatment plan 305, the devices can be any devices as described above. The devices can be selected based on the nature of the treatment plan. In a non-limiting example, a plurality of syringes can be prepared with a patient-specific amount of onabotulinumtoxinA to be delivered at each treatment site. Next, the devices can be associated with positioning devices 306. These steps 300-306 can be repeated for any number of visual staging systems, each visual staging system prepared can then be stacked 307.

FIG. 18 illustrates another embodiment of a visual staging system having three (3) stacked staging boards 132. Although one corner of the visual staging system is shown, the staging boards 132 may have four (4) standoffs 200 positioned near each corner of each staging board 132. The standoffs 200 can be generally conical in shape and be tapered so that the base of the standoff 200 narrows to a rounded end. The rounded end of the standoff 200 can be received in an aperture 202 in the staging board 132 that is dimensioned to receive the rounded end of the standoff 200. In some embodiments, the staging boards 132 do not include the aperture 202 and the rounded end of the standoff 200 contacts the top surface 136 of the staging board 132. The standoffs 200 can be secured to the bottom surface 148 of the staging board 132 using an adhesive. The standoffs 200 may comprise any suitable material such as plastic, metal, rubber, and the like. In some embodiments, the standoffs 200 can comprise a clear rubber material that provides a frictional resistance to sliding when stacked on the staging board 132 or any other surface.

FIG. 19 is a perspective view of a portion of a visual staging system according to another embodiment of the disclosure. The visual staging system has a staging board 232, which may be similar or the same in shape and size to the staging boards discussed above, including a spacer 246. The visual staging system may differ from those described above in the mechanism for connecting a clip 260 to the visual staging board 232 via a receptacle 234. The clip 260 may have a similar shape at the upper portion 262 to the upper portion 162 described above. The clip 260 is dimensioned to fit into the receptacle 234 in the staging board 232 and partially twist (e.g., ninety degrees) the clip 260 to secure the clip 260 in place in the receptacle 234. The clip 260 has a lower portion 264 that extends from a base 284 of the upper portion 262. A cylindrical arm 265 extends from the base 284 to a leg 282 that extends outwardly from the cylindrical arm 265. The leg 282 is dimensioned to be received by the receptacle 234 via an opening 235 in a top surface 236 of the staging board 232. The opening 235 is connected to a recessed area 237 of the receptacle 234 in a bottom surface 248 of the staging board 232. The recessed area 237 can take any appropriate shape to receive the leg 282 of the clip 260. The recessed area 237 may have a depth to allow the leg 282 to be received in the recessed area 237 and remain flush with the bottom surface 248 of the staging board 232.

The clip 260 is dimensioned to fit into the receptacle 234 in the staging board 232 and partially twist the clip 260 to secure the clip 260 in place in the receptacle 234. This may be achieved by orienting the leg 282 of the clip 260 to be received in the opening 235, then twisting the clip 260 so that the leg 282 is oriented in a direction that is not aligned with the opening 235. In some cases, the clip 260 can be twisted so that the leg 282 is oriented perpendicular to the opening 235 in the recessed area 237. The recessed area 237 can receive the leg 282 oriented perpendicularly to the opening 235 by providing extension walls 239, 241 that extend the recessed area 237 and allow the leg 282 to be secured in position without rotating out of position.

In yet further embodiments, the clip can include a threaded opening configured to engage a threaded male post component extending from the board, wherein the clip is rotated to threadably secure the clip and the post. In other forms, the clip can define a threaded end that extends into and/or through the board to engage a threaded recess in the board or a separate fastener (e.g., a nut) that clamps the board between the clip and the fastener, thus securing the clip to the board.

It will be appreciated by those skilled in the art that while the invention has been described above in connection with particular embodiments and examples, the invention is not necessarily so limited, and that numerous other embodiments, examples, uses, modifications, and departures from the embodiments, examples, and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A system for visual staging, the system comprising: a staging board having a plurality of receptacles spaced apart from each other and extending into a thickness of the staging board, the staging board has an anatomical image that is viewable on a top surface of the staging board; and a plurality of clips configured to be received by and extend from the plurality of receptacles such that the clips are releasably connected to the staging board; wherein the plurality of receptacles are spaced apart from each other at strategic positions on the staging board in relation to the anatomical image; wherein the plurality of clips each have an upper portion and a lower portion; the upper portion of each clip comprises a U-shaped profile that is open from above the clip such that the upper portion of the clip is configured to receive a device in a central opening of the clip; the lower portion of each clip comprises a central slot positioned between two legs, the legs each having an upper ledge for contacting a bottom surface of the staging board.

2. The system for visual staging of claim 1, wherein:
the staging board has at least one spacer attached to a surface of the board.

3. The system for visual staging of claim 2, wherein:
the at least one spacer provides spacing between the staging board and a second staging board such that the staging board and the second staging board are stackable.

4. The system for visual staging of claim 1, wherein: the anatomical image is of an anatomical structure of a human face.

5. The system for visual staging of claim 1, wherein:
a first set of the plurality of receptacles are arranged parallel with and along a longitudinal axis of the staging board and a second set of the plurality of receptacles are offset from and arranged at an angle with respect to the longitudinal axis of the staging board.

6. The system for visual staging of claim 1, wherein:
the staging board has a dry erase marker finish on the top surface of the staging board.

7. The system for visual staging of claim 1, wherein:
the staging board comprises a clear polycarbonate material.

8. The system for visual staging of claim 1, wherein:
the plurality of receptacles comprise openings formed through the thickness of the staging board.

9. The system for visual staging of claim 1, wherein
the plurality of clips are interchangeable.

10. A system for visual staging, the system comprising: a staging board having a plurality of clips spaced apart from each other at positions correlated to anatomical features depicted on an anatomical image that is viewable on a top surface of the staging board, wherein the plurality of clips extend away from the top surface of the staging board and are configured to releasably secure a treatment device, wherein the plurality of clips each have an upper portion and a lower portion; the upper portion of each clip comprises a U-shaped profile that is open from above the clip such that the upper portion of the clip is configured to receive a device in a central opening of the clip; the lower portion of each clip comprises a central slot positioned between two legs, the legs each having an upper ledge for contacting a bottom surface of the staging board.

11. The system for visual staging of claim 10, wherein:
the anatomical image is of an anatomical structure of a human face.

12. The system for visual staging of claim 10, further comprising:
at least one spacer attached to a surface of the staging board;
the at least one spacer provides spacing between the staging board and a second staging board such that the staging board and the second staging board are stackable.

13. The system for visual staging of claim 10, wherein: a first set of the plurality of securing devices are arranged parallel with and along a longitudinal axis of the staging board and a second set of the plurality of securing devices are offset from and arranged at an angle with respect to the longitudinal axis of the staging board.

14. The system for visual staging of claim 10, wherein:
the plurality of clips are received in receptacles located at the positions correlated to the anatomical features.

* * * * *

UNITED STATES PATENT AND TRADEMARK OFFICE
CERTIFICATE OF CORRECTION

PATENT NO.         : 10,813,714 B2
APPLICATION NO.    : 15/994423
DATED              : October 27, 2020
INVENTOR(S)        : Ryan Heath et al.

Page 1 of 1

It is certified that error appears in the above-identified patent and that said Letters Patent is hereby corrected as shown below:

In the Claims

Claim 13, Column 12, Line 17, "securing devices" should be --clips--.

Claim 13, Column 12, Line 19, "securing devices" should be --clips--.

Signed and Sealed this
Twenty-ninth Day of December, 2020

Andrei Iancu
*Director of the United States Patent and Trademark Office*